(12) United States Patent
Szafranski et al.

(10) Patent No.: US 6,287,844 B1
(45) Date of Patent: Sep. 11, 2001

(54) COMPOSITIONS AND METHODS FOR CONTROLLING GENETICALLY ENGINEERED ORGANISMS

(75) Inventors: Przemyslaw Szafranski, Houston, TX (US); Charlene Mello, Rochester, MA (US); Takeshi Sano, Waltham, MA (US); Cassandra L. Smith, Boston, MA (US); David L. Kaplan, Stow, MA (US); Charles R. Cantor, Boston, MA (US)

(73) Assignees: The Trustees of Boston University, Boston, MA (US); The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/019,966

(22) Filed: Feb. 6, 1998

Related U.S. Application Data

(60) Provisional application No. 60/036,935, filed on Feb. 6, 1997, now abandoned.

(51) Int. Cl.$^7$ ........................................ C12N 1/20
(52) U.S. Cl. ................................ 435/252.33; 235/252.3
(58) Field of Search ............................ 435/252.3, 252.33

(56) References Cited

U.S. PATENT DOCUMENTS 5,679,533 * 10/1997 Szafranski et al. ................... 435/7.2
5,681,745 * 10/1997 Szafranski et al. ................... 435/325

FOREIGN PATENT DOCUMENTS

WO 96/34954 * 11/1996 (WO) .

OTHER PUBLICATIONS

Marqués, S & Ramos, J. L., "Transcription control of the *Pseudomonas putida* TOL plasmid catabolic pathways," *Mol. Microbiol.* 9:923–929 (1993).

Contreras et al., "Conditional–Suicide Containment System for Bacteria which Mineralize Aromatics, " *Appl. Environ. Microbiol.* 57:1504–1508 ( 1991).

Moffat et al. "T7 Lysozyme Inhibits Transcription by T7 RNA Polymerase," *Cell* 49:221–227 (1987).

Eguchi, Y. et al., "Antisense RNA, " *Annu. Rev. Biochem.* 60:631–652 (1991).

Molin, S. et al., "Conditional Suicide System for Containment of Bacteria and Plasmids, " *Bio/Technology* 5:1315–1318 (1987).

Jensen, L. B. et al., "A Substrate–Dependent Biological Containment System for *Pseudomonas putida* Based on the *Escherichia coli gef* Gene," Appl. Environ. Microbiol. 59:3713–3717 (1993).

Kloos, D.–U. et al., "Inducible Cell Lysis System for the Study of Natural Transformation and Environmental Fate of DNA Released by Cell Death," J. Bacteriol. 176:7352–7361 (1994).

D'az, E. et al., "Universal barrier to lateral spread of specific genes among microorganisms," Mol. Microbiol. 13:855–861 (1994).

Ahrenholtz, I. et al., "A Conditional Suicide System in Escherichia coli Based on the Intracellular Degradation of DNA," Appl. Environ. Microbiol. 60:3746–3751 (1994).

Recorbet, G. et al., "Conditional Suicide System of Escherichia coli Released into Soil That Uses the *Bacillus subtilis sacB* Gene, " Appl.Environ. Microbiol. 59:1361–1366 (1993).

* cited by examiner

*Primary Examiner*—Remy Yucel
(74) *Attorney, Agent, or Firm*—Nixon Peabody LLP

(57) ABSTRACT

Compositions and methods for the control of genetically engineered organisms are described. A more effective cell suicide approach is contemplated based on the conditional expression of the lethal *Streptomyces avidinii* streptavidin gene. Toxicity of streptavidin is derived from its exceptionally high binding affinity for an essential prosthetic group, D-biotin. The general requirement for biotin through the living world makes streptavidin-based conditional lethal designs applicable to a broad range of containment strategies.

5 Claims, 5 Drawing Sheets

COMPOSITIONS AND METHODS FOR CONTROLLING GENETICALLY ENGINEERED ORGANISMS

This application claims priority from provisional patent application Ser. No. 60/036,935, filed Feb. 6, 1997, now abandoned.

This invention was made with government support under DOD Grant DAAH04-94-2004. The U.S. government has certain rights in the invention.

FIELD OF THE INVENTION

This invention relates to controlling genetically engineered organisms in the open environment, and in particular, the containment of microorganisms, including but not limited to microorganisms that degrade organic compounds such as aromatic hydrocarbons.

BACKGROUND

Genetically engineered organisms are useful in a variety of settings. Genetically engineered plants offer more efficient sources of food and fuel. Genetically engineered microorganisms (GEMs) offer unlimited supplies of medically useful proteins and also are of interest in the field of bioremediation.

Bioremediation involves the breakdown of toxic compounds by microorganisms and/or their products. Bioremediation is considerably more attractive than merely transporting wastes, as it offers the possibility of degrading toxic compounds to harmless reaction products.

Bioremediation field trials have involved both in-situ and ex-situ treatment methods. Typically, ex-situ treatment involves the transfer of contaminated waste from the site into a treatment tank designed to support microbial growth, i.e., a "bioreactor". The reactor provides for effective mixing of nutrients and control over temperature, pH and aeration to allow optimum microbial growth.

In-situ treatment involves adding biologicals directly to the waste. This avoids the problems associated with handling (e.g., pumping) toxic compounds. However, in-situ treatment has its own problems. Unlike bioreactors, where microbial growth can be monitored and adjusted, in-situ environmental conditions are difficult to measure and control.

Indeed, it is generally difficult to predict the behavior of genetically engineered organisms in natural ecosystems. There is a concern about the uncontrolled spread of recombinant DNA, including but not limited to the spread of recombinant DNA among indigenous bacterial populations. Potential risk associated with deliberate or unintentional release of GEMs into the open environment can be minimized by the use of debilitated strains. An alternative, and perhaps more appropriate approach is the introduction of conditional or stochastic maintenance functions into GEMs (Molin (1993) Curr. Opin. Biotechnol. 4:299–305; Molin et al. (1993) Annu. Rev. Microbiol. 47:139–166; Ramos et al. (1995) Bio/Technology 13:35–371-3). In such a case, the viability of GEMs depends on the expression of an essential gene or on the repression of a lethal gene controlled by a regulatory promoter responding to changes in the chemical or physical constitution of the environment, or by a promoter undergoing recombinational switches. However, the effectiveness of suicide systems is limited by relatively high frequency of their mutational inactivation, resulting in positive selection of uncontained clones.

Thus, there is a need for better control mechanisms. Such improved approaches should provide better regulation of recombinant gene expression and permit control over the spread of recombinant DNA.

SUMMARY OF THE INVENTION

This invention relates to controlling genetically engineered organisms in the open environment, and in particular, the containment of microorganisms, including but not limited to microorganisms that degrade organic compounds such as aromatic hydrocarbons. The present invention contemplates new killing genes and improved strategies to control their expression. The present invention offers a universal conditional lethal system based on the tightly regulated derepression of the streptavidin gene (stv) (Argara-a et al. (1986) Nucleic Acids Res. 14:1871–1882) from the actinobacterium *Streptomyces avidinii*. It targets the metabolism of one-carbon units at the oxidation level of carbon dioxide by depleting an essential prosthetic group, D-biotin (vitamin H); the invention can be used to complement cell suicide systems for which direct targets are cell membranes and walls, or nucleic acids.

In a preferred embodiment, any incompletely repressed expression of the stv gene is eliminated at the level of its transcription, targeting directly the RNA polymerase, as well as at the level of its translation by antisense mRNA. This novel regulatory strategy for containment of GEMs is found to have excellent performance.

It is not intended that the present invention be limited by the specific recombinant organism to be controlled. Indeed, it is not intended that the present invention be limited to hydrocarbon-degrading bacterium. A variety of bacterial and non-bacterial recombinant organisms can be controlled in this manner.

In one embodiment, the present invention contemplates a microorganism comprising a streptavidin gene under control of a promoter, said promoter being negatively regulated by a repressor protein, said repressor protein synthesized in response to an environmental signal (such as the presence of compounds to be degraded). In another embodiment, the present invention contemplates a microorganism comprising a streptavidin gene under control of a first heterologous promoter, said streptavidin gene capable of being transcribed by a heterologous RNA polymerase, said RNA polymerase expressed from a RNA polymerase gene under control of a second heterologous promoter, said second heterologous promoter inhibited by the expression of a repressor protein from a repressor gene, said repressor gene under the control of a third heterologous promoter, said repressor protein expressed by said microorganism in response to an environmental signal (such as the presence of compounds to be degraded). In yet another embodiment, the present invention contemplates a microorganism comprising a streptavidin gene under control of a first heterologous promoter, said streptavidin gene capable of being transcribed by a heterologous RNA polymerase, said RNA polymerase expressed from a RNA polymerase gene under control of a second heterologous promoter, said second heterologous promoter inhibited by the expression of a repressor protein from a repressor gene, said repressor gene under the control of a third heterologous promoter and operably linked to nucleic acid capable (upon transcription) of producing antisense RNA complementary to at least a portion of said streptavidin gene, said first heterologous promoter, or both, said repressor protein expressed by said microorganism in response to an environmental signal (such as the presence of compounds to be degraded).

It is not intended that the present invention be limited to particular polymerases or promoters. In one embodiment, the bacteriophage T7 RNA polymerase is used and the microorganism expresses the polymerase inhibitor, T7 lysozyme.

It is also not intended that the present invention be limited to a particular repressor protein. In one embodiment, the repressor is the *Escherichia coli* LacI repressor.

The present invention also contemplates methods of recombinantly producing the above-described microorganisms by linked the above-described elements in operable combination using recombinant means, as well as compositions comprising the constructs generated by said recombinant means. Finally, the present invention contemplates methods wherein the above-described microorganisms are exposed to the appropriate environment (e.g. a waste source) to cause expression of said repressor protein.

DEFINITIONS

To facilitate understanding of the invention, a number of terms are defined below.

The term "gene" refers to a DNA sequence that comprises control and coding sequences necessary for the production of a polypeptide or precursor thereof. The polypeptide can be encoded by a full length coding sequence or by any portion of the coding sequence so long as the desired activity is retained.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "recombinant nucleic acid molecule" as used herein refers to a nucleic acid (e.g. DNA) molecule which is comprised of segments joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5', i.e. upstream, of the coding region However, enhancer elements can exert their effect even when located 3' of the promoter element and the coding region. Transcription termination and polyadenylation signals are located 3' or downstream of the coding region.

Transcriptional control signals in eucaryotes comprise "promoter" and "enhancer" elements. Promoters and enhancers consist of short arrays of DNA sequences that interact specifically with cellular proteins involved in transcription (e.g., transcription factors) [Maniatis, T. et al., Science 236:1237 (1987)]. Promoter and enhancer elements have been isolated from a variety of eucaryotic sources including genes in yeast, insect and mammalian cells and viruses (analogous control elements, i.e., promoters, are also found in procaryotes). The promoter and enhancer elements which direct transcription of a linked gene are generally located 5' or upstream of the coding region. However, enhancer elements can exert their effect even when located 3' of the promoter element and the coding region.

The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The terms "in operable combination" "operably linked" and grammatical equivalents as used herein refers to the linkage of nucleic acid sequences in such a manner that a nucleic acid molecule capable of directing the synthesis of a desired protein molecule is produced. The term also refers to the linkage of amino acid sequences in such a manner that a functional protein is produced.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The term "microorganism" as used herein means an organism too small to be observed with the unaided eye and includes, but is not limited to bacteria, viruses, protozoans, fungi, and ciliates.

The term "microbial gene sequences" refers to gene sequences derived from a microorganism.

The term "bacteria" refers to any bacterial species including abacterial and archaebacterial species.

The term "expression vector" or "vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

A "waste source" can be a solid or liquid waste source (e.g., paper pulp, pulp mill effluent, sludge, wastewater, petroleum spill, etc.).

DESCRIPTION OF THE INVENTION

This invention relates to controlling genetically engineered organisms in the open environment, and in particular, the containment of microorganisms, including but not limited to microorganisms that degrade organic compounds such as aromatic hydrocarbons. The killing function of the present invention is based on the almost irreversible binding ($K_d$~$10^{-5}$ M) of D-biotin by streptavidin (Weber et al. (1989) Science 243:85–88), a tetrameric protein produced by *S. avidinii*. Cell death results from depletion of free biotin and direct inhibition of biotin-dependent carboxylases, decarboxylases and transcarboxylases (Fall (1979) Methods Enzymol. 62:390–398). Inactivation of these enzymes blocks the first committed step of fatty acid biosynthesis and affects gluconeogenesis, amino acid metabolism, replenishment of the Krebs cycle, and substrate uptake by some anaerobes.

Figure 1:
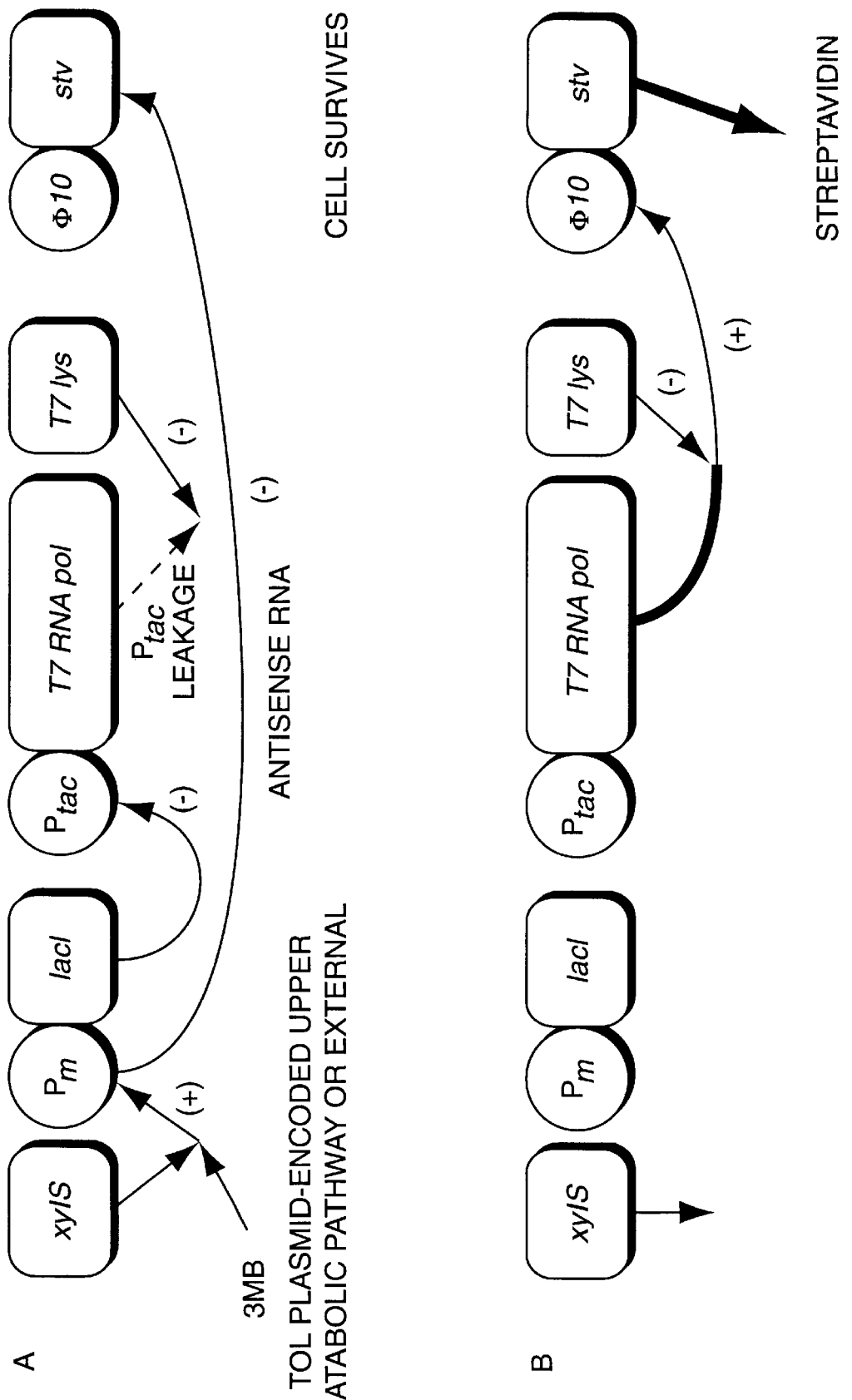
FIGS. 1A and 1B shows one embodiment of a scheme of a tightly regulated biological containment system to control survival of bacteria by availability of 3MB or other hydrocarbon effectors of the XylS protein. (A) survival; (B) induction of a lethal phenotype.

One strategy for using streptavidin as a suicide factor comprises placing its gene directly under the control of a promoter negatively regulated by a repressor protein synthesized in response to an environmental signal. The most serious drawback of such a design is incomplete repression (leakiness) of regulatory promoters. To achieve tighter control of the induction of a lethal phenotype, additional regulatory circuits, involving a heterologous RNA polymerase and its inhibitor, can be employed by coupling expression of the stv gene to the bacteriophage T7 transcription system (Studier et al. (1990) Methods Enzymol. 185:60–89) (FIG. 1). In this case, the stv gene was transcribed from the T7 gene 10 promoter ($\phi$10) by T7 RNA polymerase. The T7 gene 1, encoding RNA polymerase, was fused to the *E. coli* hybrid trp-lac (tac) promoter, negatively regulated by the LacI repressor. The *E. coli* LacI-O$_{lac}$ system has been shown to be active in a broad range of microorganisms, including *P. putida* (Bagdasarian et al. (1983) Gene 26:273–282) and yeasts (Amore et al. (1991) Gene 109:89–97). The leakiness of the P$_{tac}$ promoter was compensated by an inhibitor of T7 RNA polymerase, T7 lysozyme (Moffat and Studier (1987) Cell 49:221–227). The lysozyme, in addition to its muramidase activity, binds to T7 RNA polymerase and blocks its transcription activity (the T7 lysozyme maintains its T7 RNA polymerase inhibition ability in a heterologous *P. putida* system). The T7 gene 3.5, encoding lysozyme, was constitutively transcribed from the P$_{tet}$ promoter. The lacI gene was transcribed from the P$_m$ promoter induced by XylS protein-aromatic carboxylic acid complexes. Both the P$_m$ promoter and xylS regulatory gene (used xylS2 allele encodes XylS$^{thr45}$ with altered effector specificity and increased affinity for benzoates) are derived from the *P. putida* TOL plasmid where they control expression of genes clustered in the meta-cleavage pathway operon (Marques and Ramos (1993) Mol. Microbiol. 9:923–929). Streptavidin should be synthesized upon inactivation of LacI with IPTG or by interception of LacI synthesis in response to depletion of a benzoic acid effector of the XylS protein, such as 3MB. Positive effectors of the XylS protein can be taken up by *P. putida* or produced within the cell by oxidation of toluene, m- and p-xylenes, and their derivatives, through the TOL-encoded upper catabolic pathway (3MB from m-xylene) (Marques and Ramos (1993) Mol. Microbiol. 9:923–929). Note that the bacteriophage T7 system, in the configuration described above, by itself causes stress to the cell when induced. Transcription from the strong $\phi$10 and P$_{tac}$ promoters, and overexpression of T7 RNA polymerase, for example, engage a large pool of ribonucleotides, and subsequently amino acyl tRNAs, and ribosomes.

Figure 2A:
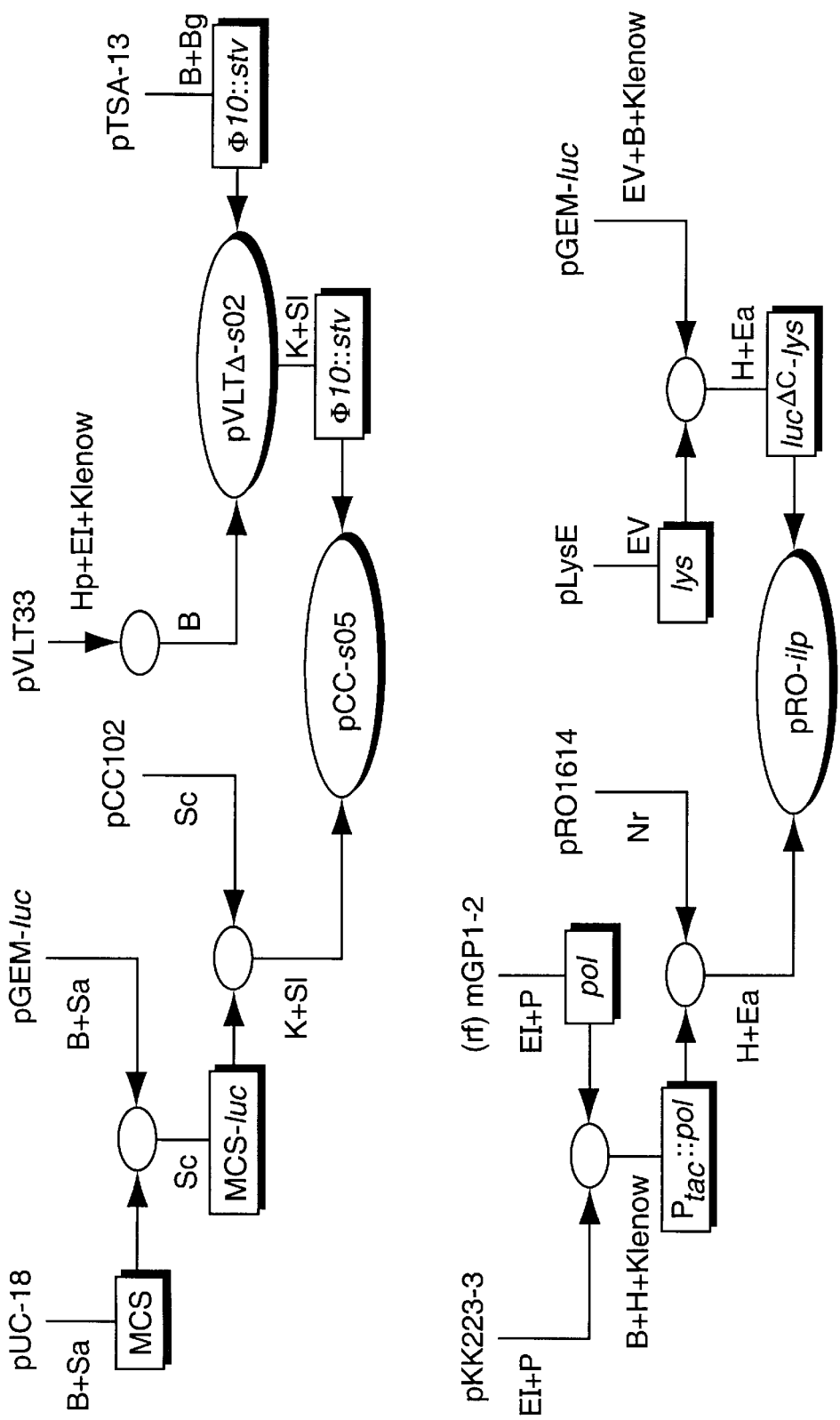
FIGS. 2A and 2B shows one approach to the construction of plasmids pCC-s05 and pRO-ilp (A), and physical maps of their killing and regulatory elements (B). stv or s, streptavidin gene; T7 RNA pol or pol, T7 RNA polymerase gene (T7 gene 1); lys, T7 lysozyme gene (T7 gene 3.5); kan, kanamycin-resistance gene; luc$^{Ac}$, a truncated luc gene encoding an N-terminal fragment of luciferase; MCS, a fragment of pUC 18 containing part of the multiple cloning site. Restriction enzymes and their cleavage sites: B, BamH I; Bg, Bgl I; D, Dra I; Ea, Eag I; El, EcoR I; EV, EcoR V; H, Hind III; Hp, Hpa I; K, Kpn I; N, Nhe I; Nr, Nru I; P, Pst I; Sa, Sca I; Sc, Sac I; Sl, Sal I; Sm, Sma I. Unique cleavage sites are marked with asterisks.
Figure 2B:
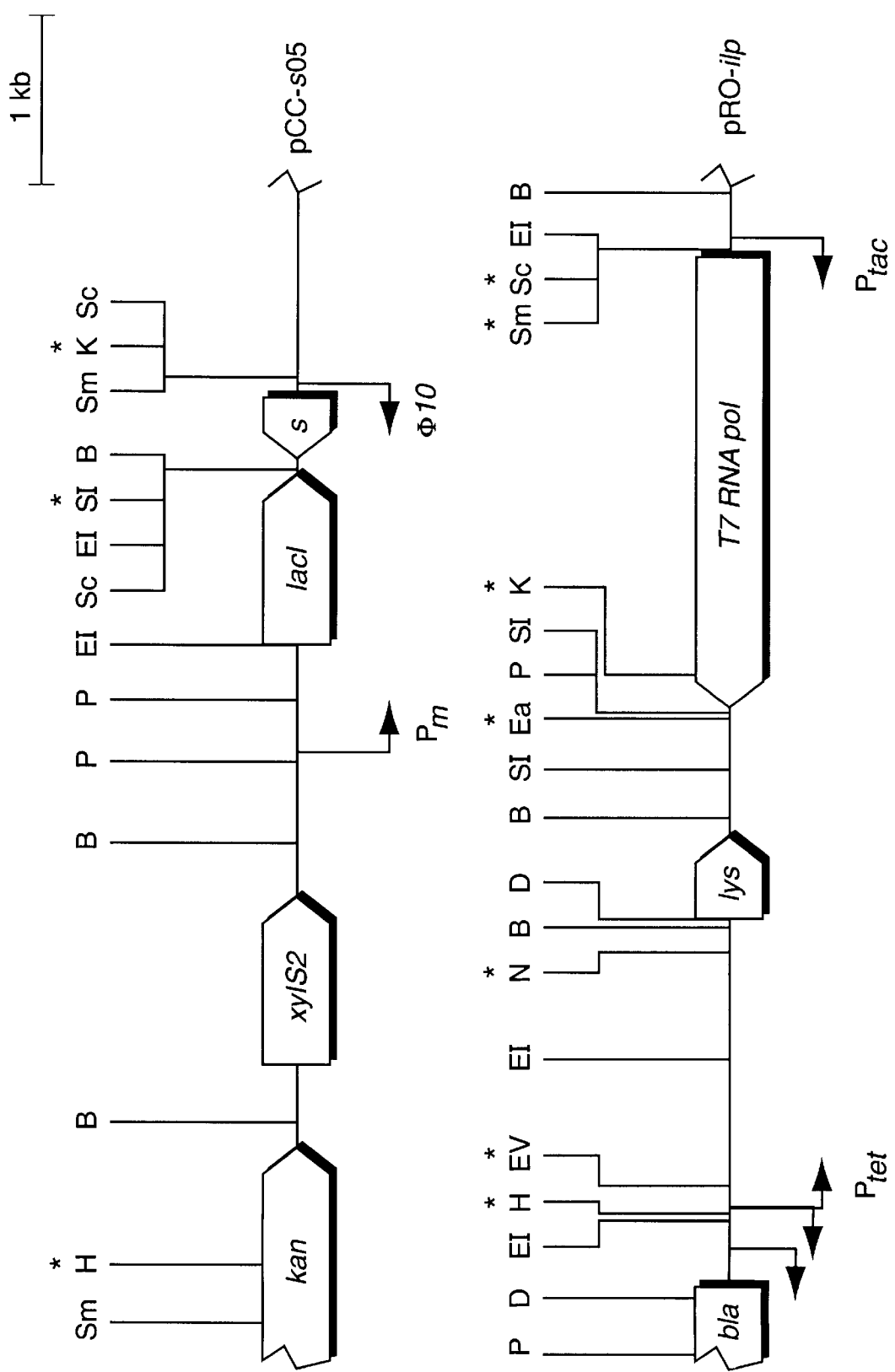

An additional level of regulation of stv gene expression was achieved by placing the $\phi$10::stv fusion immediately downstream of the lacI gene, but in the opposite orientation (FIGS. 1 and 2B). This should further decrease uninduced expression of the stv gene by generating an antisense RNA (Eguchi et al. (1991) Annu. Rev. Biochem. 60:631–652) complementary to the stv transcript. On the other hand, RNA synthesized from $\phi$10 promoter upon induction of suicide should similarly block the remaining laci mRNA and improve the kinetics of bacterial culture decay.

The T7 lysozyme and T7 RNA polymerase genes are also oppositely oriented. However, in this case, the level of accumulating countertranscript is likely to be lower because of the distance between P$_{tet}$ and P$_{tac}$ promoters (ca 6-kb).

The entire system was tested in the Gram-negative soil rod *Pseudomonas putida* potentially useful for bioremediation of areas polluted with aromatic hydrocarbon-based organic solvents and petroleum. A containment system for pseudomonads is of particular importance because their nutritional versatility for low molecular weight organic compounds and fast growth rates allow them to rapidly colonize a wide range of habitats and predominate in soil or water microflora. Coupling this system to regulatory elements derived from the *P. putida* TOL catabolic plasmid (Marques and Ramos (1993) Mol. Microbiol. 9:923–929) conditioned survival of bacteria only in the presence of an aromatic carboxylic acid which they can degrade.

So far, there are only a few genes that have been proven to be bactericidal upon expression in the members of genus Pseudomonas. These are genes encoding cell membrane destabilizing peptides Hok (*E. coli* plasmid R1) (Molin et al. (1987) Bio/Technology 5:1315–1318) and Gef (*E. coli*) (Jensen et al. (1993) Appl. Environ. Microbiol. 59:3713–3717), lysis genes of bacteriophages $\lambda$ and $\phi$X174 (Kloos et al. (1994) J. Bacteriol. 176:7352–7361), and the colE3 gene encoding an RNase (*E. coli*) (D'az et al. (1994) Mol. Microbiol. 13:855–861).

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); gm (grams); mg (milligrams); μg (micrograms); L (liters); ml (milliliters); μl (microliters); cm (centimeters); mm (millimeters); μm (micrometers); nm (nanometers); ° C (degrees Centigrade).

Bacterial Strains, Plasmids And Culture Conditions

Subcloning was performed by using an $E.$ $coli$ K-12 strain XL1-Blue MRF' (lacI$^q$ and Tet$^r$ on F') (Stratagene). Suicide constructs were tested in $P.$ $putida$ mt-2 strain KT2440 {hsdR1} (Franklin et al. (1981) Proc. Natl. Acad. Sci. USA 78:7458–7462). DNA used was a replicative form (rf) of a bacteriophage M13 clone, mGP 1–2 (Studier et al. (1990) Methods Enzymol. 185:60–89), and plasmids pKK223-3 (Amp$^r$) (Brosius and Holy (1984) Proc. Natl. Acad. Sci. USA 81:6929–6933) (Pharmacia), pCC102 (Kan$^r$) (Contreras et al. (1991) Appl. Environ. Microbiol. 57:1504–1508), pGEM-luc (Amp$^r$) (Promega), pLysE (Cml$^r$) (Studier et al. (1990) Methods Enzymol. 185:60–89), pRO1614 (Amp$^r$, Tet$^r$) (Olsen et al. (1982) J. Bacteriol. 150:60–69), pTSA-13 (Amp$^r$) (Sano et al. (1995) J. Biol. Chem. 270:28204–28209), pUC19 (Amp$^r$), and pVLT33 (Kan$^r$) (de Lorenzo et al. (1993) Gene 123:17–24).

Bacteria were grown aerobically in LB medium at 30° C., unless otherwise stated. Antibiotics were used at the following concentrations (μg/ml): ampicillin, 100 ($E.$ $coli$) or 800 ($P.$ $putida$; optimized for this particular isolate); kanamycin, 25 ($E.$ $coli$) or 75 ($P.$ $putida$); chloramphenicol, 50 ($E.$ $coli$); and tetracycline, 10 ($E.$ $coli$). Isopropyl β-D-thiogalactopyranoside (IPTG) and m-methylbenzoate (3MB) were used at concentrations of 1 mM and 0.2 mM, respectively.

Recombinant DNA Techniques

DNA manipulations were carried out by standard procedures (Sambrook et al. (1989) Molecular Cloning: A Laboratory Manual (Cold Spring Harbor Lab., Plainview, N.Y.), 2nd Ed). $P.$ $putida$ was transformed by a RbCl method (Bagdasarian and Timmis (1982) Curr. Top. Microbiol. Immunol. 96:47–67) or by electroporation (Gene Pulser apparatus, Bio-Rad).

Construction Of Each Element Of The System

The stv gene, the $P_{tac}$ promoter, and the bacteriophage T7 transcription system, i.e., the φ10 promoter, and the RNA polymerase and lysozyme genes, were placed on two compatible plasmids, pCC102 (an RSF1010 derivative bearing the xylS2 gene and the $P_m$::lacI fusion) and pRO1614 (pMB1 and pRO1600 replicon), as shown in FIG. 2A. Fragments of pUC18 and pGEM-luc plasmids, bearing convenient cloning sites, were inserted into pCC102, downstream of the lacI gene, to facilitate subcloning of the φ10::stv fusion and subsequent DNA manipulations. The stv gene used here encodes a core streptavidin consisting of amino acid residues 16–133 of the mature streptavidin (Sano et al. (1995) J. Biol. Chem. 270:28204–28209). This protein has a higher binding stoichiometry to biotinylated macromolecules than natural core streptavidin. A 1.3-kb fragment of the luc gene, derived from pGEM-luc, was inserted into pRO1614 as a spacer to reduce expression of the T7 lysozyme gene. This also makes the construct comparable to the corresponding region of pRO-llp, in which the lysozyme gene is separated from the $P_{tet}$ promoter by the 1-kb lacI gene (lacI inserted between the EcoR I and BamH I sites of the Tet$^r$ locus).

For construction of pCC-s04 carrying the lac operator ($O_{lac}$) immediately upstream of φ10::stv, a Bgl II-Hind III fragment of pTSA-13 carrying φ10::stv was first inserted into the Sma I-Hind III site of pKK223-3. Then, a BamH I fragment carrying $O_{lac}$φ10::stv was cloned into the BamH I site of pVLT33. Finally, a Kpn I-Sal I fragment of the resulting plasmid was placed in the Kpn I-Sal I site of pCC-s05.

Fluctuation Tests

Frequency of the appearance of clones resistant to the induction of cell death was estimated following the Luria-Delbruick approach as described elsewhere (Knudsen and Karlstrom (1991) Appl. Environ. Microbiol. 57:85–92).

Induction Of The Lethal Phenotype

Figure 3A:
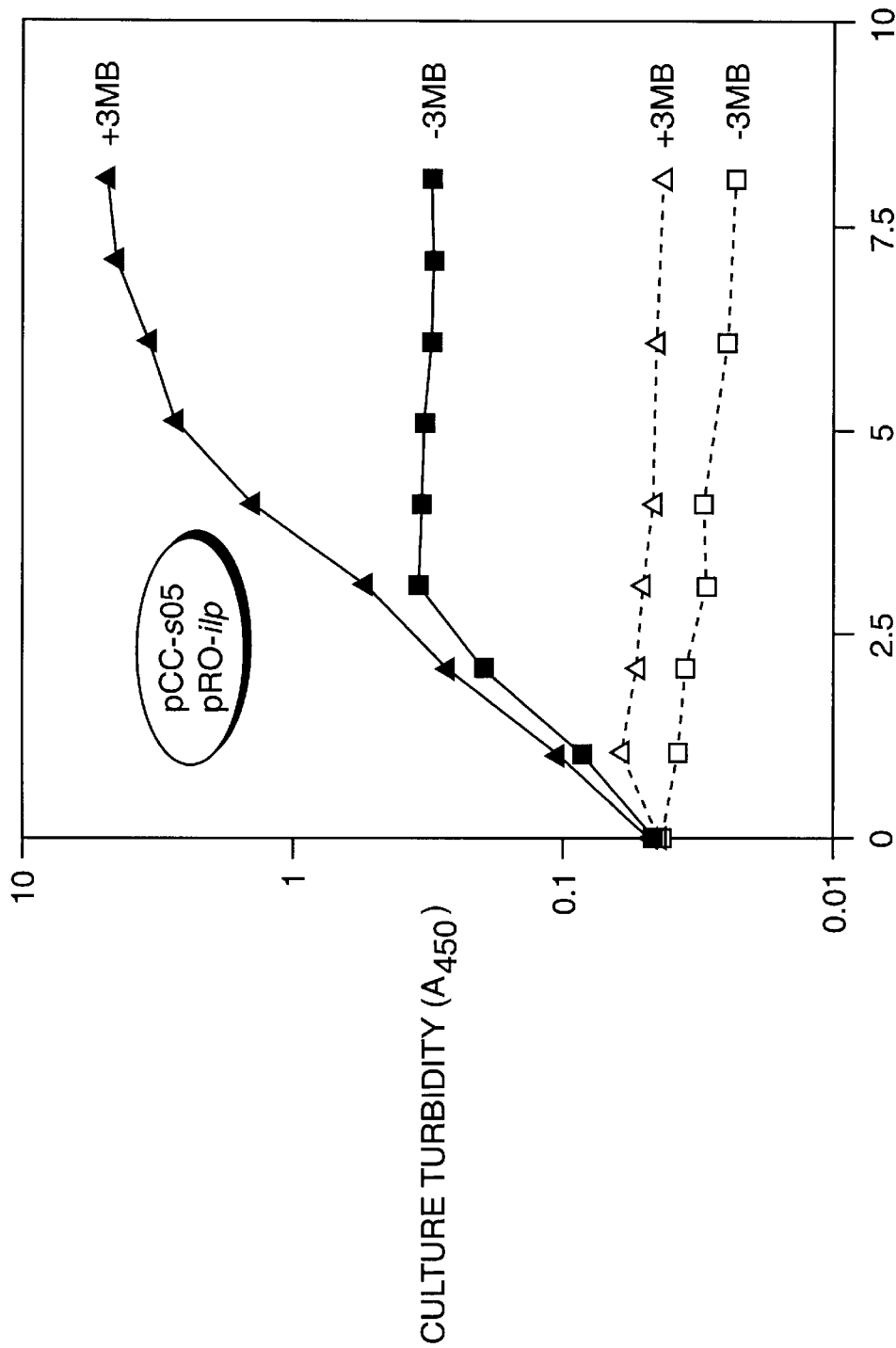
FIGS. 3A and 3B shows the kinetics of the induced suicide of *P. putida* cultures. Bacteria were grown to a mid-exponential growth phase in LB medium containing 3MB, ampicillin, and kanamycin. After washing with LB, cells were diluted 100-fold with LB supplemented with antibiotics with or without 3MB (A), or resuspended in the same medium without 3MB (B), and further incubated. Broken lines with open symbols refer to the additional presence of IPTG in LB. Plasmid combinations: s04, pCC-s04/pRO-ilp; s05, pCC-s05/pRO-ilp. CFU, colony forming unit. Each data point is the mean of 2 or 3 independent experiments.

The entire suicide construct was prepared as a pCC-s05 (xylS2, lacI, and stv genes)/pRO-ilp (T7 RNA polymerase and lysozyme genes) broad host-range two-plasmid system (FIG. 2). Copy numbers of pCC-s05 and pRO-ilp in $P.$ $putida$ were estimated to be 1–3 and 10–20, respectively. Transfer of $P.$ $putida$ (pCC-s05, pRO-ilp) from a 3MB-containing medium to a 3MB-free medium resulted in inhibition of the culture growth within 3 hours at 30° C. (FIG. 3A). Replacement of the stv gene with a truncated gene encoding only the N-terminal half of the protein or the use of pCC102 plasmid lacking the φ10::stv fusion, instead of pCC-s05, caused almost no response of $P.$ $putida$ to the absence of 3MB inducer.

Figure 3B:
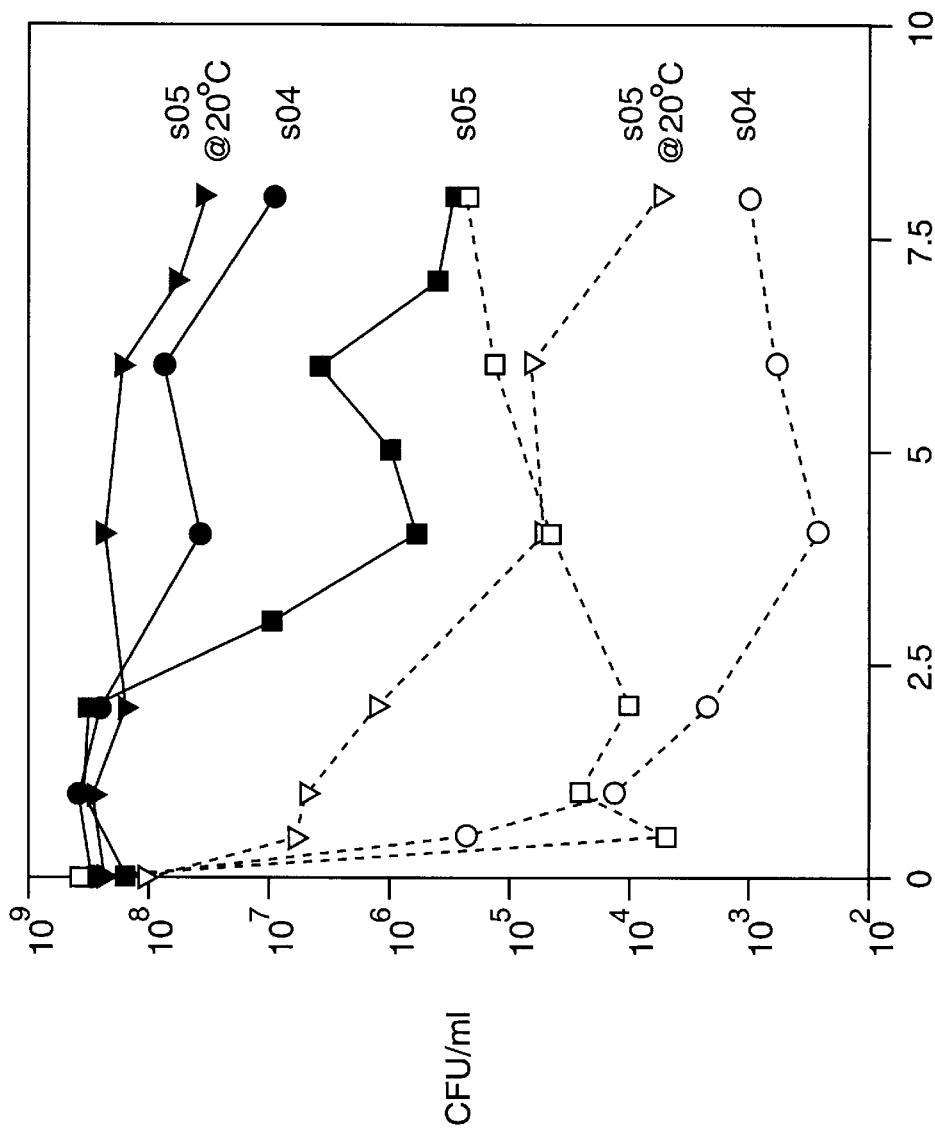

The efficiency of host cell killing by intracellularly synthesized streptavidin was quantitated by counting viable cells before and after the removal of 3MB (FIG. 3B). Bacterial samples were periodically collected and incubated for a week on agar plates supplemented with 3MB, 50 μg/ml biotin, and appropriate antibiotics. At 4–8 hours after induction of the stv gene expression by the removal of 3MB, up to 99.9% of the $P.$ $putida$ cells did not renew growth even after prolonged incubation in the presence of biotin. Longer incubation times were needed to contain the culture at lower temperatures. For example, 8–9 hours were required to reduce the bacterial population by 90% at 20° C. As expected, removal of 3MB, together with the addition of IPTG, induced faster and more efficient cell death.

Replacement of pCC-s05 with pCC-s04 containing the $O_{lac}$ (with $P_{tac}$) 41 bp upstream of φ10, at the edge of the DNA sequence covered by a promoter-bound T7 RNA polymerase, resulted in remarkably slower killing upon removal of 3MB. However, in the additional presence of IPTG it resulted in killing of as much as 6 orders of magnitude of the initial bacterial population in 4 hours. This represents one of the most rapid and efficient eliminations of a bacterial culture reported. Derepression of $P_{tac}$ preceding φ10 on pCC-s04 by removal of 3MB did not induce a lethal level of the stv gene expression by bacterial RNA polymerase, presumably because of the presence of a putative transcription terminator/attenuator immediately downstream of φ10 and residual antisense expression in the absence of 3MB. The need for the T7 lysozyme also in $P.$ $putida$ with the $O_{lac}$φ10 fusion on pCC-s04 was verified by removing the lysozyme gene from pRO-ilp (cutting the plasmid with Sph I and religating). Although the resulting $P.$ $putida$ (pCC-s04, pRO-ip) was virtually contained upon removal of 3MB, the cell population grew very slowly, and the accumulation of mutants was significantly higher.

Rates of escape of $P.$ $putida$ from killing were estimated by fluctuation tests. Table 1 compares bacteria carrying plasmid constructs (i) producing different uninduced basal levels of active T7 RNA polymerase, i.e., with and without T7 lysozyme (pCC-s04/pRO-ilp or pCC-s04/pRO-ip), (ii) with or without direct LacI-$O_{lac}$-dependent accessibility of the φ10 promoter for RNA polymerase (pCC-s05/pRO-ilp or pCC-s04/pRO-ilp), and (iii) with or without countertranscript protection against basal expression of the stv gene (pCC-s05/pRO-ilp and pVLTA-s02/pRO-ilp). The construction of pVLTA-s02 is shown in FIG. 2A. pRO-ilp differs from pRO-ilp by having the pCC102-derived lacI gene instead of a 1.3-kb luc DNA spacer. The level of accumulation of killing-resistant clones in *P. putida* with the pCC-s05/pRO-ilp plasmid combination was about two orders of magnitude lower than in the construct without antisense expression, although pCC- and pVLT-based hybrid plasmids (both RSF1010 derivatives) are not completely isogenic. For the pCC-s04/pRO-ilp combination, which has the $O_{lac}$ also next to φ10, killing-resistant mutants appeared with the lowest frequency. The absence of T7 lysozyme within a cell increased the level of mutation by two orders of magnitude.

TABLE 1

Survival of *P. putida*, carrying different constructs for protection against uninduced expression of the stv gene, upon induction of suicide. Each arrow indicates the direction of transcription. T, bacterial transcription terminator; $O_{lac}$, lac operator.

| Plasmid combination | Surroundings of the stv gene | Survival per cell per generation |
| --- | --- | --- |
| pVLTA-s02, pRO-llp | $T \xleftarrow{kan} T \xleftarrow{stv} \Phi 10$ | $10^{-4}$–$10^{-5}$ |
| pCC-s05, pRO-ilp | $P_m \xrightarrow{lacI} \xleftarrow{stv} \Phi 10$ | $10^{-6}$–$10^{-7}$ |
| pCC-s04, pRO-ilp | $P_m \xrightarrow{lacI} \xleftarrow{stv} \Phi 10, O_{lac}$ | $10^{-7}$–$10^{-8}$ |
| pCC-s04, pRO-ip | $P_m \xrightarrow{lacI} \xleftarrow{stv} \Phi 10, O_{lac}$ | $10^{-5}$–$10^{-6}$ |

Restriction nuclease cleavage analysis of plasmids from twenty killing-resistant clones showed, in most cases, changes in DNA digestion patterns involving the stv and T7 RNA polymerase gene regions.

The rate of inactivation, a basic determinant of the efficiency of suicide designs, in our stv-based system is $10^{-7}$–$10^{-8}$ per cell per generation. This value is lower than those already reported for constructs based on single toxic functions ($10^{-2}$–$10^{-6}$), even in *E. coli*, which is easier to contain (Contreras et al. (1991) Appl. Environ. Microbiol. 57:1504–1508; Jensen et al. (1993) Appl. Environ. Microbiol. 59:3713–3717; Ahrenholtz et al. (1994) Appl. Environ. Microbiol. 60:3746–3751; Recorbet et al.(1993) Appl. Environ. Microbiol. 59:1361–1366). It apparently reflects the very low basal level of streptavidin in cells. Despite the fact that the coupled T7 transcription/LacI-$O_{lac}$ system is less leaky than the lac system alone (Table 1), an additional explanation of the better protection of cells against uninduced expression of the stv gene is synthesis of the antisense RNA originating from the $P_m$ promoter. The lack of such protection, especially without a transcription terminator (e.g., LacI-$O_{lac}$ complex) upstream of φ10 as in pVLTA-s02, resulted in a remarkably higher mutation frequency of $10^{-4}$–$10^{-5}$ per cell per generation. The LacI-$O_{lac}$ complex formed upstream of the φ10 in pCC-s04 apparently interferes also with binding of bacteriophage RNA polymerase to the φ10 promoter (slower induction of the stv gene expression upon removal of 3MB) and further decreases the frequency of appearance of killing-resistant clones by reducing uninduced transcription of the stv gene. Preliminary data on the killing of *E. coli* by IPTG-induced expression of the stv gene suggest that, as expected, this system should be effective also in enteric bacteria.

A temperature shift from 30° C. to 20° C. alters the kinetics of the culture decay. This effect was more pronounced in a bacterial population depleted of 3MB in the absence of IPTG, indicating a contribution of both weaker interaction of T7 RNA polymerase with φ10 and the longer lifetime of the LacI repressor and/or its mRNA within a cell. Continuing decline of the culture after the addition of IPTG indicates a lower rate of mutational inactivation of the construct at 20° C. than at 30° C.

The suicide design was tested under rich nutrient conditions, i.e., in LB medium containing some biotin. The growth conditions were favorable for cell survival, since killing occurs by depletion of biotin. In fact, slightly higher levels of IPTG-induced cell death were observed in minimal M9 medium. Under mostly starving conditions in, for instance, soil or seawater, this system may perform even more effectively. A Sma I fragment of pCC-s05 containing xylS2, lacI and stv genes (FIG. 2B) has been already stable integrated into *P. putida* chromosome via mini-Tn5 mediated transposition. Other known killing genes can be placed under control of φ10 promoter and integrated into the chromosome of *P. putida* {hsdR1 stv lacI xylS2 Kan$^r$} to create multiple back up systems following incorporation of the T7 RNA polymerase-lysozyme regulatory module. Alternatively, stability of pRO-ilp upon induction of suicide in the absence of selection for plasmid maintainence can be achieved, for instance, by inserting into it the parB (hok/sok) locus of R1.

From the above, it should be clear that the present invention provides an approach that utilizes additional regulatory circuits arranged to reduce the basal level of the expression of killing gene can remarkably increase the effectiveness of cell suicide machinery. Because of the general demand of biotin as a carboxyl carrier in the living world, the stv gene can serve as a universal cassette for programmed cell death. The stv-based system in combination with, for example, biotinylated solid supports and biotinylated fluorescent probes could also allow very sensitive monitoring of the presence of recombinant microorganisms.

What is claimed is:

1. A microorganism, comprising a streptavidin gene under control of a first heterologous promoter, wherein said streptavidin gene is by a heterologous RNA polymerase, said RNA polymerase expressed from a RNA polymerase gene under control of a second heterologous promoter, said second heterologous promoter inhibited by the expression of a repressor protein from a repressor gene, said repressor gene is under the control of a third heterologous promoter and operably linked to nucleic acid encoding antisense RNA complementary to at least a portion of said streptavidin gene, said repressor protein expressed by said microorganism in response to aromatic hydrocarbons.

2. The microorganism of claim 1, wherein said microorganism is a bacterium.

3. The microorganism of claim 1, wherein said repressor protein is the *Escherichia coli* LacI repressor.

4. The microorganism of claim 1, wherein said heterologous RNA polymerase comprises the bacteriophage T7 RNA polymerase.

5. The microorganism of claim 4, wherein said microorganism expresses T7 lysozyme.

* * * * *